(12) United States Patent
Amino et al.

(10) Patent No.: US 7,244,462 B2
(45) Date of Patent: Jul. 17, 2007

(54) AMINO ACID DERIVATIVE AND SWEETENING AGENT

(75) Inventors: Yusuke Amino, Kawasaki (JP); Kazuko Hirasawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 448 days.

(21) Appl. No.: 10/981,587

(22) Filed: Nov. 5, 2004

(65) Prior Publication Data

US 2005/0118317 A1    Jun. 2, 2005

(30) Foreign Application Priority Data

Nov. 5, 2003    (JP)    ............................. 2003-376033

(51) Int. Cl.
*A23L 1/236*    (2006.01)

(52) U.S. Cl. ...................... 426/548; 426/534; 426/650; 548/469

(58) Field of Classification Search ..................... None
See application file for complete search history.

(56) References Cited

OTHER PUBLICATIONS

U.S. Appl. No. 10/992,795, filed Nov. 22, 2004, Amino et al.
U.S. Appl. No. 10/981,587, filed Nov. 5, 2004, Amino et al.

*Primary Examiner*—Cecilia Tsang
*Assistant Examiner*—Robert Havlin
(74) *Attorney, Agent, or Firm*—Oblon, Spivak, McClelland, Maier & Neustadt, P.C.

(57) ABSTRACT

The present invention provides a novel amino acid derivative, and a salt for thereof. The present invention further provides a sweetening agent and a food or beverage, which contains the novel amino acid derivative of the present invention to increase the sweetness of the same.

22 Claims, No Drawings

AMINO ACID DERIVATIVE AND SWEETENING AGENT

CROSS-REFERENCE TO RELATED APPLICATIONS

The present application claims priority to Japanese Application No. JP 2003-376033, filed on Nov. 5, 2003, which is hereby incorporated by reference in its entirety.

BACKGROUND OF THE INVENTION

1. Field of the Invention

The present invention provides a novel amino acid derivative, and a salt for thereof. The present invention further provides a sweetening agent and a food or beverage, which contains the novel amino acid derivative of the present invention to increase the sweetness of the same.

2. Discussion of the Background

In recent years, there has been an increased incidence of problems resulting from excessive ingestion of sugar, for example obesity and various types of diseases accompanied thereby. Therefore, development of a low-calorie sweetening agent to serve as a sugar substitute is in high demand. In addition to strength of the sweetness, several additional characteristics and requirements should also be satisfied by the sugar-substitute including: low-calorie, high safety (i.e., little or no side effects), high stability against heat or acid, excellent sweetness quality, and low cost.

Currently, several types of sweetening agents have been used or proposed. For example, aspartame has gained notoriety as a widely used sweetening agent, due to its potent sweetness strength and quality as well as its ease for industrial manufacture on a large scale and its excellent safety. Furthermore, studies on aspartame derivatives have also been extensively conducted. In addition thereto, sweetening materials having various characteristics have been proposed as a sweetening agent and investigations toward the practical use thereof have been conducted. Additional sweetening agents that are currently used include naturally occurring thaumatin, glycyrrhizin, stevioside and the like which are derived from plants and can be collected on a large scale.

Although not yet being used practically as a sweetening agent, monatin has been known as a natural sweetening material. Monatin is a naturally occurring amino acid derivative isolated from root bark of *Schlerochiton ilicifolius* which is a self-sown plant in the Northwestern Transvaal region of South Africa, and R. Vleggaar et al. (J. Chem. Soc. Perkin Trans., 3095-3098, (1992)), reported its structure as being (2S,4S)-2-amino-4-carboxy-4-hydroxy-5-(3-indolyl) pentanoic acid ((2S,4S)-4-hydroxy-4-(3-indolylmethyl)-glutamic acid (see, Chemical formula (3)). Additionally, according to Vleggar et al. the degree of sweetness of the (2S,4S) isomer referred to as being derived from this natural plant has been reported to be 800 times, or maybe 1400 times of sucrose. However, a study of the relationship between the chemical structure of monatin and the appearance of the sweetness has not been performed. Thus, it has not been elucidated as to which functional group is required for the sweetness of monatin. Accordingly, no attempt has been conducted to obtain a novel sweetening material by using monatin as a lead compound and modifying the chemical structure.

[Chemical formula 3]

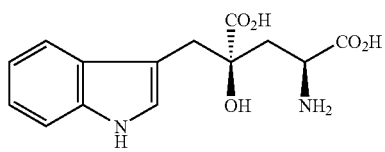

(3)

Although some processes for the synthesis of monatin have been reported, a suitable industrial process has not been reported to date. Examples of synthesis of monatin can be found in South Africa (ZA) Patent Application No. 87/4288, C. W. Holzapfel et al., Synthetic Communications, 24 (22), 3197-3211 (1994), U.S. Pat. No. 5,994,559, and K, Nakamura et al., Organic Letters, 2, 2967-2970 (2000). Therefore, a derivative having a sweetness strength equivalent to or greater than that of monatin, which can be more readily produced than monatin, is desired and would have more feasible practicability as a sweetening agent.

The aforementioned South Africa (ZA) Patent Application No. 87/4288 discloses that monatin produces intramolecular lactone or lactam through cyclodehydration under a specified condition. It is not clear whether these cyclized products have sweetness or not. However, assuming that these cyclized products do not have sweetness, it is believed that derivatives of monatin that do not yield or are difficult to yield such products are more preferred sweetening materials in terms of stability when used as a sweetening agent.

On the other hand, D-6-chlorotryptophan has been known as a sweetening material, which has an amino acid structure similarly to monatin in terms of the chemical structure. Among the analogs thereof, known amino acids exhibiting sweetness are limited only to compounds having a substituent at an indole ring of tryptophan (see, JP-A-S48-16624).

Therefore, elucidation of a chemical structure required to impart sweetness of monatin is desired, as well as determining the chemical structure of a sweetening agent having superior properties required for a sweetening agent than conventional sweetening materials.

SUMMARY OF THE INVENTION

It is an object of the present invention to provide a novel amino acid derivative which is excellent in stability and safety, and is comparative or much superior to monatin and existing sweetening agents in terms of degree of sweetness.

Another object of the present invention is to provide a low-calorie sweetening agent, a food, beverage or the like containing the amino acid derivative of the present invention as an effective ingredient.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in chemistry, enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention provides a novel sweetening agents which are derived from and/or structurally similar to monatin and salts thereof.

In connection with monatin represented by the above formula (3), the present inventors synthesized compounds in which structural transformation or chemical modification of each functional group were undertaken, and various properties in addition to strength of sweetness were examined. As a result, among the compounds whose hydroxyl group and carboxyl group, which are substituents at position-4 of monatin, are substituted with other functional group, i.e., compounds represented by the following general formula (1), it was found that compounds having one of various substituents in $R_1$ and $R_2$ as defined herein have strong sweetness. The present inventors also found that these derivatives can be readily used for sweetening agents, foods or beverages and the like. On the basis of such a variety of findings, the present invention was accomplished.

More specifically, an embodiment of the present invention is an amino acid derivative represented by the following formula (1) or a salt form thereof and a sweetening agent and other product such as a food or beverage to which sweetness is imparted, which comprises the same.

[Chemical formula 1]

(1)

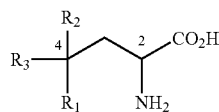

In the above formula (1), $R_1$ represents any substituent selected from a hydrogen atom, a hydroxyl group, an alkyl group having 1 to 3 carbon atoms, an alkoxy group having 1 to 3 carbon atoms, and a hydroxylalkyl group having 1 to 3 carbon atoms;

$R_2$ represents any substituent selected from an alkyl group having 1 to 3 carbon atoms, a hydroxylalkyl group having 1 to 3 carbon atoms, a carbamoyl group, a carbamoyl group having an alkyl having 1 to 3 carbon atoms (—CO—NH—CH$_3$ and the like), and a carboxyl group; and $R_3$ represents a substituent represented by the following formula (2).

[Chemical formula 2]

(2)

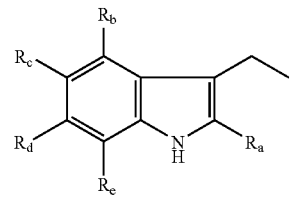

In the above formula (2), $R_a$, $R_b$, $R_c$, $R_d$, and $R_e$ each independently represent any substituent selected from a hydrogen atom, a hydroxyl group, an alkyl group having 1 to 3 carbon atoms, and an alkoxy group having 1 to 3 carbon atoms; wherein $R_b$ and $R_c$, and/or $R_d$ and $R_e$ may together form an alkylene group having 1 to 4 carbon atoms (methylene group and the like), respectively.

In a preferred embodiment, the compounds of the present invention are isolated and/or purified.

However, compounds concurrently having $R_1$ of a hydroxyl group, $R_2$ of a carboxyl group, and $R_3$ of a 3-indolylmethyl group in the formula (1) are excluded from the derivative.

In a preferred embodiment, examples of the amino acid derivative of the invention include the derivatives as described above, where in the above formula (1), $R_1$ represents a hydrogen atom, a hydroxyl group, a methyl group, or a methoxy group; $R_2$ represents a methyl group, an ethyl group, a hydroxymethyl group, a 1-hydroxyethyl group, a 2-hydroxyethyl group, a carbamoyl group, an N-methylcarbamoyl group, an N-ethylcarbamoyl group, or a carboxyl group; and $R_3$ represents a 3-indolylmethyl group, a 3-(5-methylindolyl)methyl group, a 3-(6-methylindolyl)methyl group, a 3-(5-hydroxyindolyl)methyl group, or a 3-(6-chloroindolyl)methyl group, however, compounds concurrently having $R_1$ of a hydroxyl group, $R_2$ of a carboxyl group, and $R_3$ of a 3-indolylmethyl group in the formula (1) are excluded from said derivative.

In formula (1) above, the configuration of the carbon atoms at position 2 and position 4 is not particularly limited, which may be any one of (R), (S) and (RS).

When the amino acid derivative of the present invention is in the form of a salt, the actual kind of salt is not limited. In addition, when the derivative is used in a food or beverage, in particular, and when the derivative having a form of a salt is used, any salt acceptable in a food or beverage can be adopted.

Also, in another embodiment of the present invention is a sweetening agent, or a food or beverage, or other product to which sweetness is imparted, wherein at least one of the aforementioned derivatives of the present invention is added as an effective ingredient. In this instance, at least one carrier and/or bulking agent for a sweetening agent may be included.

The derivative of the present invention as defined by formula (1) may be used on its own as an effective ingredient or may be used with one or more additional compounds defined by formula (1). Further, in one kind of the derivative for use (one compound), a free form, a form of a salt (one kind or more), or a mixture thereof may be adopted. In case of multiple kinds, a free form, a form of a salt (one kind or more), or a mixture thereof may be adopted for each compound.

The novel amino acid derivative, or salt form thereof, of the present invention has strong sweetness, with a sweetness quality similar to that of sugar. Particularly, (2R,4R)-2-amino-4-hydroxy-4-ethylcarbamoyl-4-(3-indolylmethyl)butyric acid and the like exhibit a high degree of sweetness and stability. Therefore, a low-calorie sweetening agent having superior safety and the degree of sweetness compared to conventional sweetening agents; a food or beverage having sweetness imparted using this sweetening agent, and the like can be provided.

Examples of the preferable compound to be involved in the amino acid derivative of the invention include the followings.

[1] Compounds represented by formula (1) above

Note, however, that in the above formula (1), $R_1$ represents any substituent selected from a hydrogen atom, a hydroxyl group, an alkyl group having 1 to 3 carbon atoms, an alkoxy group having 1 to 3 carbon atoms, and a hydroxylalkyl group having 1 to 3 carbon atoms.

$R_2$ represents any substituent selected from an alkyl group having 1 to 3 carbon atoms, a hydroxylalkyl group having 1 to 3 carbon atoms, a carbamoyl group, a carbamoyl group having an alkyl having 1 to 3 carbon atoms (—CO—NH—CH$_3$ and the like), and a carboxyl group.

$R_3$ represents a substituent represented by the above formula (2).

In the formula (2) above, $R_a$, $R_b$, $R_c$, $R_d$, and $R_e$ each independently represent any substituent selected from a hydrogen atom, a hydroxyl group, an alkyl group having 1 to 3 carbon atoms, and an alkoxy group having 1 to 3 carbon atoms; wherein $R_b$ and $R_c$, and/or $R_d$ and $R_e$ may together form an alkylene group having 1 to 4 carbon atoms (methylene group and the like), respectively.

However, compounds concurrently having $R_1$ of a hydroxyl group, $R_2$ of a carboxyl group, and $R_3$ of a 3-indolylmethyl group in the formula (1) are excluded from the derivative.

[2] The compound according to the above item [1] wherein, in the above formula (1), $R_1$ represents a hydrogen atom, a hydroxyl group, a methyl group, or a methoxy group; $R_2$ represents a methyl group, an ethyl group, a hydroxymethyl group, a 1-hydroxyethyl group, a 2-hydroxyethyl group, a carbamoyl group, an N-methylcarbamoyl group, an N-ethylcarbamoyl group, or a carboxyl group; and $R_3$ represents a 3-indolylmethyl group, a 3-(5-methylindolyl)methyl group, a 3-(6-methylindolyl)methyl group, a 3-(5-hydroxyindolyl)methyl group, or a 3-(6-chloroindolyl)methyl group, however, compounds concurrently having $R_1$ of a hydroxyl group, $R_2$ of a carboxyl group, and $R_3$ of a 3-indolylmethyl group in the formula (1) are excluded from said derivative.

[3] The compound according to the above item [1] or [2] wherein, in the above formula (1), configuration of the carbon atom at position 2 is any one of (R), (S) and (RS).

[4] The compound according to the above item [1] or [2] wherein, in the above formula (1), configuration of the carbon atom at position 4 is any one of (R), (S) and (RS).

[5] The compound according to the above item [1] wherein, in the above formula (1), $R_1$ represents a hydrogen atom; $R_2$ represents a carboxyl group; and $R_3$ represents a 3-indolylmethyl group, and wherein configuration of the carbon atoms at position 2 and position 4 is (R), (S) or (RS).

[6] The compound according to the above item [1] wherein, in the above formula (1), $R_1$ represents a hydroxyl group; $R_2$ represents a carboxyl group; and $R_3$ represents a 3-(6-methylindolyl)methyl group, and wherein configuration of the carbon atoms at position 2 and position 4 is (R), (S) or (RS).

[7] The compound according to the above item [1] wherein, in the above formula (1), $R_1$ represents a hydroxyl group; $R_2$ represents a hydroxymethyl group; and $R_3$ represents a 3-indolylmethyl group, and wherein configuration of the carbon atoms at position 2 and position 4 is (R), (S) or (RS).

[8] The compound according to the above item [1] wherein, in the above formula (1), $R_1$ represents a hydroxyl group; $R_2$ represents a methyl group; and $R_3$ represents a 3-indolylmethyl group, and wherein configuration of the carbon atoms at position 2 and position 4 is (R), (S) or (RS).

[9] The compound according to the above item [1] wherein, in the above formula (1), $R_1$ represents a hydroxyl group; $R_2$ represents an ethyl group; and $R_3$ represents a 3-indolylmethyl group, and wherein configuration of the carbon atoms at position 2 and position 4 is (R), (S) or (RS).

[10] The compound according to the above item [1] wherein, in the above formula (1), $R_1$ represents a hydroxyl group; $R_2$ represents a carbamoyl group; and $R_3$ represents a 3-indolylmethyl group, and wherein configuration of the carbon atoms at position 2 and position 4 is (R), (S) or (RS).

[11] The compound according to the above item [1] wherein, in the above formula (1), $R_1$ represents a hydroxyl group; $R_2$ represents an N-methylcarbamoyl group; and $R_3$ represents a 3-indolylmethyl group, and wherein configuration of the carbon atoms at position 2 and position 4 is (R), (S) or (RS).

[12] The compound according to the above item [1] wherein, in the above formula (1), $R_1$ represents a hydroxyl group; $R_2$ represents an N-ethylcarbamoyl group; and $R_3$ represents a 3-indolylmethyl group, and wherein configuration of the carbon atoms at position 2 and position 4 is (R), (S) or (RS).

[13] The compound according to the above item [1] wherein, in the above formula (1), $R_1$ represents a hydrogen atom, or a hydroxyl group; $R_2$ represents a methyl group, an ethyl group, a hydroxymethyl group, a carbamoyl group, an N-methylcarbamoyl group, an N-ethylcarbamoyl group, or a carboxyl group; and $R_3$ represents a 3-indolylmethyl group, or a 3-(6-methylindolyl)methyl group, and wherein configuration of the carbon atoms at position 2 and position 4 is (R), (S) or (RS).

The derivative of the invention involves any form of various kinds of salts that may be present for the aforementioned compound.

The invention further involves the followings as another mode thereof.

[14] A sweetening agent, or a food or beverage, or other product to which sweetness is imparted, which comprises at least one of the aforementioned derivatives of the invention (which may include the aforementioned compound and any salt thereof) as an effective ingredient. In this case, at least one of carriers and bulking agents for a sweetening agent may be included.

[15] A process for imparting sweetness at to a product (food or beverage, pharmaceutical product, intraoral sanitary product or the like) that requires sweetness by including (mixing, adding) least one of the aforementioned amino acid derivatives of the invention (which may include the aforementioned compound and any salt thereof).

The derivative of the present invention involves compounds represented by formula (1) and salts thereof, and examples of the salts thereof include alkali metal salts with sodium, potassium or the like; alkaline earth metal salts with calcium, magnesium or the like; ammonium salts with ammonia or the like; salts with an amino acid such as lysine and arginine; salts with an inorganic acid such as hydrochloric acid and sulfuric acid; salts with an organic acid such as citric acid and acetic acid; and salts with other sweetening agent or a sweetening agent ingredient which may include saccharin, acesulfame, cyclamic acid and glycyrrhizic acid, and the like. These salts are involved in the derivative of the invention as described above.

For preparing these salts, any conventional or known step of forming a salt may be utilized. For example, an intended salt can be readily prepared by allowing the compound (free form) involved in the aforementioned derivative of the invention to react with acid, alkali, the aforementioned sweetening agent or the like in a suitable solvent such as water.

The derivative of the invention, i.e., the compound and the form of the salt thereof of the invention was proven to have strong sweetness with a quality of sweetness that is similar to sugar, as a result of a sensory test. For example, the degree of sweetness of 2-amino-4,5-dihydroxy-4-(3-indolylmethyl)pentanoic acid (mixture of the (2S,4S) isomer and (2R,4R) isomer at a ratio of 1:1) was about 1250 times as high as that of sugar, and the degree of sweetness of (2R,4R)-2-amino-4-hydroxy-4-ethylcarbamoyl-4-(3-indolylmethyl)butyric acid was about 1600 times as high as that of sugar. Further, the half life of (2R,4R)-2-amino-4-hydroxy-4-ethylcarbamoyl-4-(3-indolylmethyl)butyric acid in an aqueous acidic solution (in a citrate buffer solution of pH=3, at 70° C.) was about 97 hrs, which was more stable in comparison with aspartame (half life: about 35 hrs). Structure and results of the sensory test on several synthesized amino acid derivatives (represented by the following formula (1)) are presented in Table 1.

[Chemical formula 1]

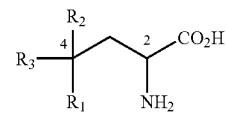

(1)

TABLE 1

Structure and multiplying power of sweetness of amino acid derivative

| Compound No. | $R_1$ | $R_2$ | $R_3$ | Configuration[1] | Degree of sweetness[2] |
|---|---|---|---|---|---|
| 1 | H | $CO_2H$ | 3-indolylmethyl | RS:RR = 3:1 | about 200 |
| 2 | OH | $CO_2H$ | 3-(6-methylindolyl)methyl | RR:SS:RS:SR = 3:3:2:2 | about 650 |
| 3 | OH | hydroxymethyl | 3-indolylmethyl | RR:SS = 1:1 | about 1250 |
| 4 | OH | hydroxymethyl | 3-indolylmethyl | RS:SR = 1:1 | about 750 |
| 5 | OH | $CH_3$ | 3-indolylmethyl | Isomer ratio = 3:3:2:2 | about 900 |
| 6 | OH | $CH_2CH_3$ | 3-indolylmethyl | Isomer ratio = 3:3:2:2 | about 500 |
| 7 | OH | $CONHCH_3$ | 3-indolylmethyl | RR | about 200 |
| 8 | OH | $CONHCH_2CH_3$ | 3-indolylmethyl | RR | about 1600 |

[1]Configuration at position 2 and position 4; Example: (2R,4S) = RS. The ratio of presence was determined with $^1$H-NMR.
[2]Compared with a 4 to 5% sucrose solution.

In Table 1 above, "H" represents a hydrogen atom; "OH" represents a hydroxyl group; "$CH_3$" represents a methyl group; "$CH_2CH_3$" represents an ethyl group; "$CONHCH_3$" represents an N-methylcarbamoyl group; and "$CONHCH_2CH_3$" represents an N-ethylcarbamoyl group. In the section of configuration, "RS" represents "(2R,4S)"; and "RR" represents "(2R,4R)". Furthermore, "RS:RR=3:1" represents "the ratio of (2R,4S) to (2R,4R) being 3:1".

When the amino acid derivative of the invention, or a salt form thereof, is used as a sweetening agent, as a matter of course, one or more additional sweetening agents may be combination as long as no particular problem occurs (i.e., the additional sweetening agent does not compromise the safety and sweetness of the compound of the present invention). Examples of other sweetening agents include, but are not limited to, a saccharide, aspartame, acesulfame K, sucralose, and monatin.

When the derivative of the invention is used as a sweetening agent, a carrier and/or an bulking agent may be used as needed. The carrier and/or the bulking agent may be any conventionally known carrier or bulking agent. Examples of the carrier and bulking agent include, but are not limited to, polydextrose, starch, maltodextrines, cellulose, methylcellulose, carboxymethylcellulose, and other cellulose derivatives, sodium alginate, pectins, gums, lactose, maltose, glucose, sucrose, leucine, glycerol (glycerole), mannitol, sorbitol (sorbitole), xylitol, erythritol, and equivalents thereof and the like, which may be used alone or in any combination thereof.

The amino acid derivative of the present invention may be used as a sweetening agent alone or as an ingredient of a sweetening agent. Further, the amino acid derivative of the present invention can be used as a sweetening agent for products such a foods or beverages to which sweetness is desired. Examples of such foods and beverages include, but are not limited to, confectioneries, chewing gums, sanitary goods, cosmetics, medicaments, food or products for non-human animals, and various types of veterinary products. Moreover, the derivative of the invention can be used in the form of a product containing the derivative of the invention, to which sweetness is imparted, as well as in the process for imparting sweetness to the product to which sweetness is desired or required. The process for using the inventive amino acid derivatives (e.g., adding to foods or beverages) is not particularly limited and includes any conventional or known method, which are commonly used as a process for using a sweetening agent.

Therefore, the present invention provides a method of increasing the sweetness of a food or beverage comprising mixing an effective amount of the sweetening agent of the present invention with a food, beverage, or precursor thereof.

The amino acid derivative according to the present invention may be utilized as a safe sweetening agent having a high degree of sweetness and excellent stability, and having a similar structure to that of naturally occurring monatin. Therefore, development of novel sweetening agents and foods or beverages to which sweetness is imparted, which comprises the derivative is prominently useful in food industry.

In the present invention, it is to be understood that the content of the active ingredient (i.e., the inventive derivatives of formula (1)) in the sweetening agent/composition, as well as foods or beverages containing the same, can be adjusted as taste and texture dictate. However, in an embodiment of the present invention the concentration of the derivatives of formula (1) range from 0.0006 to 0.15% by weight, preferably from 0.003 to 0.075% by weight.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES $^1$H-NMR spectra were acquired with a Bruker AVANCE400 (400 MHz), and MS spectra were acquired with a Thermo Quest TSQ700.

Example 1

Synthesis of (2R,4S)-2-Amino-4-(3-indolyl)methyl Pentandioic Acid 1

[Chemical formula 5]

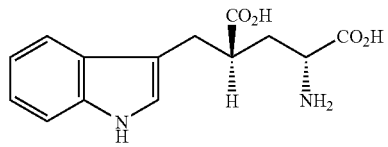

In an atmosphere of argon, 457 mg of (D)-N-t-butoxy-carbonylpyroglutamic acid methyl ester (1.88 mmol) was dissolved in 5 ml of anhydrous tetrahydrofuran (THF). The reaction solution was maintained at a temperature of −78° C., and 1.1 ml of a 1 mol solution (29%, solution in THF) of lithium hexamethyldisilazide (LHMDS) was added thereto. One hour later, 5 ml of a solution of 700 mg of N-t-butoxycarbonyl-3-bromomethylindole (2.26 mmol) in THF was added thereto, and stirred at −78° C. for 2 hrs. To the reaction solution a saturated aqueous ammonium chloride solution was added, followed by extraction with 50 ml of ethyl acetate (twice). The resulting organic layer was washed with a saturated salt solution, and dried over anhydrous magnesium sulfate. The magnesium sulfate was removed by filtration, and the resulting filtrate was concentrated. The residue was purified on a preparative thin layer chromatography (PTLC) to give 380 mg of methyl(2R,4S)-N-t-butoxycarbonyl-4-(3-indolyl)methyl-pyroglutamate (0.80 mmol) as a viscous oily product (ratio of (2R,4S)-isomer to (2R,4R)-isomer was 4:1).

Methyl(2R,4S)-N-t-butoxycarbonyl-4-(3-indolyl)methyl-pyroglutamate (380 mg) was dissolved in a mixed solution of 5 ml of isopropanol and 5 ml of water to form a reaction solution. To the reaction solution 539 mg of lithium hydroxide monohydrate (12.86 mmol) was added followed by stirring at room temperature overnight. After vacuum concentrating the reaction solution, 2 N hydrochloric acid was added to adjust the pH of the solution to 2 to 3, followed by extraction with 50 ml of ethyl acetate (twice). The resulting organic layer was washed with a saturated NaCl solution, and dried over anhydrous magnesium sulfate. The magnesium sulfate was removed by filtration, and the filtrate was concentrated. The residue was washed with hexane, and dried under a reduced pressure.

The residue was then dissolved in 3 ml of formic acid, and the solution was maintained at a temperature of 0° C., to which 2 ml of a 4 N hydrochloric acid solution in dioxane was added. After stirring the reaction solution at room temperature for 30 min, the solution was vacuum concentrated. After washing the residue with ether followed by vacuum concentration, 5 ml of water was added thereto, and the insoluble substances were removed by filtration. The filtrate was adsorbed on about 15 ml of a strongly acidic ionic exchange resin (Amberlite IR120B H AG; manufactured by Organo Corporation), and eluted with 5% aqueous ammonia. After concentrating the eluate, the concentrate was freeze dryied resulting in 96 mg of (2R,4S)-2-amino-4-(3-indolyl)methyl pentandioic acid (0.35 mmol) as pale yellow powder (Compound No. 1 in Table 1).

MS Spectrum—
 ESI-MS: 277.25 (M+H)$^+$, 275.06 (M−H)$^−$.

NMR Spectrum—

$^1$H-NMR (D$_2$O, 400 MHz) δppm:

[Isomer A (80%)] 1.83-1.91 (1H,m), 2.08-2.16 (1H,m), 2.65-2.73 (1H,m), 2.85-2.92 (1H,m), 2.30-2.36 (1H,m), 3.64 (1H,m), 7.08 (1H,t), 7.15 (1H,s), 7.16 (1H,t), 7.41 (1H,d), 7.64 (1H,d).

[Isomer B (20%)] 1.92-2.00 (1H,m), 2.25-2.30 (1H,m), 2.75-2.80 (1H,m), 2.85-2.92 (1H,m), 2.30-2.36 (1H,m), 3.51 (1H,m), 7.08 (1H,t), 7.15 (1H,s), 7.16 (1H,t), 7.41 (1H,d), 7.64 (1H,d).

Degree of Sweetness—

About 200 times (compared with a 5% sugar solution).

Example 2

Synthesis of 4-Hydroxy-4-(6-methylindole-3-ylmethyl)glutamic Acid 2

[Chemical formula 6]

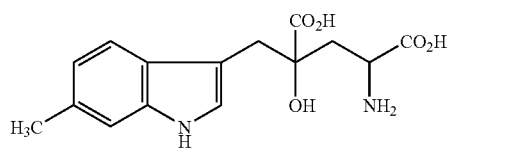

6-Methylindole-3-pyruvic acid in an amount of 3.40 g (15.65 mmol) and oxalacetic acid in an amount of 12.4 g (93.9 mmol) were suspended in 40 ml of water, and maintained at a temperature of 0° C. A solution of 12.3 g of potassium hydroxide (219.1 mmol) dissolved in 20 ml of water was added to the suspension. After stirring the reaction solution overnight at room temperature, 4.35 g of hydroxylammonium chloride (62.6 mmol) was added thereto followed by additional stirring at room temperature for one day. Concentrated hydrochloric acid was added to the reaction solution to adjust the pH of 2 to 3, followed by extraction with 100 ml of ethyl acetate (three times). The organic layer was washed with 100 ml of water and 100 ml of a saturated salt solution, and dried over anhydrous magnesium sulfate. The magnesium sulfate was removed by filtration, and the filtrate was vacuum concentrated. The residue was dissolved in 10 ml of ethanol, and 2 ml of 28% aqueous ammonia was added thereto at 0° C. After vacuum concentrating the reaction solution, the concentrate was crystallized using ethanol-toluene to give about 700 mg of 4-[3-(6-methylindolyl)methyl]-4-hydroxy-2-hydroxyimino glutalic acid.ammonium salt as powder.

The aforementioned 4-[3-(6-methylindolyl)methyl]-4-hydroxy-2-hydroxyimino glutalic acid.ammonium salt in an amount of 340 mg and 5% rhodium carbon (Rh—C) in an amount of 170 mg were suspended in 20 ml of aqueous ammonia, and reduced overnight at room temperature in an atmosphere of hydrogen at 11 atm. The catalyst was removed by filtration, and the filtrate was vacuum concentrated. Following washing with ethyl acetate, the residue was vacuum concentrated. The washed residue was dissolved in 5 ml of water, and adsorbed on about 30 ml of a strongly acidic ionic exchange resin (Amberlite IR120B H AG; manufactured by Organo Corporation), and eluted with 5% aqueous ammonia. After concentrating the eluate, the concentrate was freeze dried resulting in 100 mg of a stereoisomer mixture of 4-hydroxy-4-(6-methylindole-3-yl-methyl)glutamic acid (0.31 mmol) as pale yellow powder (Compound No. 2 in Table 1, with a small amount of 6-methyltryptophan and alanine included as byproducts).

MS Spectrum—
 ESI-MS: 307.15 (M+H)$^+$, 305.06 (M−H)$^−$.

NMR Spectrum—

$^1$H-NMR (D$_2$O, 400 MHz) δppm:

[Isomer A (60%)] 1.93 (1H,dd), 2.76 (1H,d), 2.93 (1H,d), 3.18 (1H,d), 3.50-3.57 (1H,m) 6.80-6.93 (1H,m), 7.05 (1H,s), 7.19 (1H,s), 7.51 (1H,d).

[Isomer B (40%)] 2.09 (1H,dd), 2.58 (1H,d), 3.09 (2H,s), 3.75-3.80 (1H,m), 6.80-6.93 (1H,m), 7.05 (1H,s), 7.15 (1H,s), 7.36 (1H,d).

Degree of Sweetness—

About 650 times (compared with a 5% sugar solution).

Example 3

Synthesis of (2S,4S)- and (2R,4R)-2-Amino-4,5-dihydroxy-4-(3-indolylmethyl)pentanoic Acid Mixture 3

[Chemical formula 7]

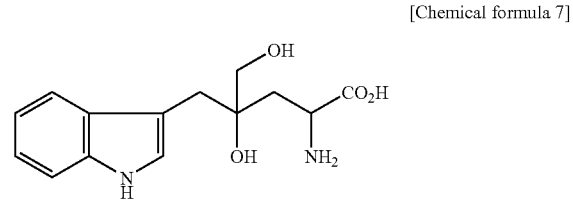

A mixture of (2S,4S)- and (2R,4R)-2-benzyloxycarbonylamino-4-carboxy-4-(3-indolylmethyl)-γ-butyrolactone in an amount of 408 mg (1.0 mmol), which was obtained by benzyloxycarbonylation and lactonization of a mixture of (2S,4S)- and (2R,4R)-monatin, was dissolved in 3 ml of THF, and 0.21 ml of triethylamine (1.5 mmol) was added thereto. The reaction solution was cooled to −18° C., and 0.20 ml of isobutyl chloroformate (1.5 mmol) was added. After stirring at −18° C. for 30 min, a solution of 113 mg of sodium borohydride (3.0 mmol) dissolved in 1.5 ml of water was added, and stirred at −18° C. for 20 min. After adding 2.0 ml of a 2 N hydrochloric acid solution, the reaction solution was vacuum concentrated. To the residue 30 ml of water was added and an extraction manipulation with 50 ml of ethyl acetate was repeated twice. The resulting organic layer was washed with 50 ml of water and 50 ml of a saturated salt solution, and dried over anhydrous magnesium sulfate. The magnesium sulfate was removed by filtration, and the filtrate was vacuum concentrated. The residue was purified on PTLC resulting in 345 mg of a mixture of (2S,4S)- and (2R,4R)-2-benzyloxycarbonylamino-4-hydroxymethyl-4-(3-indolylmethyl)-γ-butyrolactone (0.88 mmol) as a viscous oily product.

The aforementioned mixture of (2S,4S)- and (2R,4R)-2-benzyloxycarbonylamino-4-hydroxymethyl-4-(3-indolylmethyl)-γ-butyrolactone in an amount of 335 mg was dissolved in 5 ml of methanol, and 50 mg of 10% palladium carbon (Pd—C, containing 50% water) was added thereto. Following reduction at room temperature in an atmosphere of hydrogen at ordinary pressure for 2 hrs, 0.42 ml of a 2 N sodium hydroxide solution was added. The catalyst was removed by filtration, and the filtrate was vacuum concentrated. The residue was dissolved in 5 ml of water, and the solution was neutralized with a strongly acidic ionic exchange resin (Amberlite IR120B H AG). The resin was removed by filtration and the filtrate was freeze-dried resulting in 241 mg of (2S,4S)- and (2R,4R)-2-amino-4,5-dihydroxy-4-(3-indolylmethyl)pentanoic acid mixture (0.80 mmol) as powder (Compound No. 3 in Table 1).

MS Spectrum—

ESI-MS: 265.30 (M+H)$^+$, 263.10 (M−H)$^−$.

NMR Spectrum—

$^1$H-NMR (CD$_3$OD, 400 MHz) δppm: 1.84 (1H,dd), 2.28 (1H,dd), 2.91 (2H,dd), 3.61 (2H,dd), 3.84-3.88 (1H,m), 6.99-7.03 (1H,m), 7.06-7.15 (1H,m), 7.15 (1H,s), 7.33 (1H), 7.64 (1H,d).

Degree of Sweetness—

About 1250 times (compared with a 5% sugar solution).

Example 4

Synthesis of (2S,4R)- and (2R,4S)-2-Amino-4,5-dihydroxy-4-(3-indolylmethyl)pentanoic Acid Mixture 4

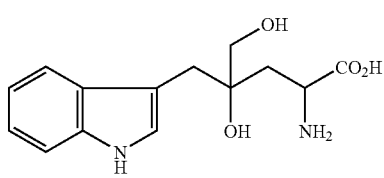

[Chemical formula 8]

In a similar manner to example 3 except that a mixture of (2S,4R)- and (2R,4S)-2-benzyloxycarbonylamino-4-carboxy-4-(3-indolylmethyl)-γ-butyrolactone was used instead of the mixture of (2S,4S)- and (2R,4R)-2-benzyloxycarbonylamino-4-carboxy-4-(3-indolylmethyl)-γ-butyrolactone, (2S,4R)- and (2R,4S)-2-amino-4,5-dihydroxy-4-(3-indolylmethyl)pentanoic acid mixture was obtained with a yield of 61.0% as powder (Compound No. 4 in Table 1).

MS Spectrum—

ESI-MS: 265.30 (M+H)$^+$, 263.10 (M−H)$^−$.

NMR Spectrum—

$^1$H-NMR (D$_2$O, 400 MHz) δppm: 1.95 (1H,dd), 2.15 (1H,dd), 2.95-3.05 (1H,m), 3.41-3.48 (2H,m), 3.89-3.93 (1H,m), 7.10 (1H,m), 7.16 (1H,m), 7.25 (1H,s), 7.45 (1H,d), 7.66 (1H,d).

Degree of Sweetness—

About 750 times (compared with a 5% sugar solution).

Example 5

Synthesis of 2-Amino-4-hydroxy-4-(3-indolylmethyl)pentanoic Acid 5

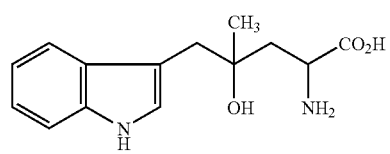

[Chemical formula 9]

3-(3-indolyl)-2-methyl-1-propene in an amount of 767 mg (4.48 mmol) prepared from indole and methallyl bromide was dissolved in 7 ml of anhydrous chloroform, and 2.1 ml of triethylamine (14.8 mmol) was added thereto. A solution of 1.36 g of ethyl chloro (hydroxylimino)acetate (8.96 mmol) dissolved in 5 ml of anhydrous chloroform was then added dropwise at room temperature over 30 min. After stirring the reaction solution for 5 hrs, 20 ml of water was added, followed by extraction with 20 ml of chloroform (twice). The chloroform layer was dried over anhydrous magnesium sulfate and then the magnesium sulfate was removed by filtration, and the filtrate was vacuum concentrated. The residue was purified on PTLC resulting in 641 mg of ethyl 5-(RS)-methyl-5-(3-indolylmethyl)-4,5-dihydroisoxazole-3-carboxylate (2.24 mmol) as a viscous oily product.

The aforementioned ethyl 5-(RS)-methyl-5-(3-indolylmethyl)-4,5-dihydroisoxazole-3-carboxylate in an amount of 641 mg was dissolved in 16 ml of ethanol, and 4 ml of water and 188 mg of lithium hydroxide monohydrate (4.48 mmol) were added followed by stirring at room temperature for one hour. The reaction solution was vacuum concentrated, and 20 ml of water was added to the residue. The pH of the solution was adjusted to 2 to 3 with a 2 N hydrochloric acid solution. Extraction of the solution with 20 ml of ethyl acetate was conducted twice, and the organic layer was dried over anhydrous magnesium sulfate. The magnesium sulfate was removed by filtration, and the filtrate was vacuum concentrated resulting in 556 mg of 5-(RS)-methyl-5-(3-indolylmethyl)-4,5-dihydroisoxazole-3-carboxylic acid as a viscous oily product.

The aforementioned 5-(RS)-methyl-5-(3-indolylmethyl)-4,5-dihydroisoxazole-3-carboxylic acid in an amount of 540 mg was dissolved in 4 ml of ethanol, and 10 ml of 28% aqueous ammonia and 300 mg of 5% Rh—C were added thereto. Reduction performed at room temperature in an atmosphere of hydrogen at 10 atm for 12 hrs. The catalyst was removed by filtration, and after vacuum concentrating the filtrate, the product was again dissolved in water followed by freeze-drying resulting in 370 mg of 2-amino-4-hydroxy-4-(3-indolylmethyl)pentanoic acid (1.41 mmol) as light brown powder (Compound No. 5 in Table 1).

MS Spectrum—

ESI-MS: 263.30 (M+H)$^+$, 261.11 (M−H)$^-$.

NMR Spectrum—

$^1$H-NMR (D$_2$O, 400 MHz) δppm:

[Isomer A (60%)] 1.15 (3H,s), 1.90 (1H,m), 2.18 (1H,dd), 2.94-2.99 (1H,m), (1H,m), 3.95 (1H,m), 7.00-7.09 (1H,m), 7.10-7.17 (1H,m), 7.21 (1H,s), 7.41 (1H,d), 7.62 (1H,d).

[Isomer B (40%)] 1.21 (3H,s), 1.87 (1H,m), 2.08 (1H,dd), 2.94-2.99 (1H,m), 3.84 (1H,d), 7.00-7.09 (1H,m), 7.10-7.17 (1H,m), 7.21 (1H,s), 7.41 (1H,d), 7.60 (1H,d).

Degree of Sweetness—

About 900 times (compared with a 5% sugar solution).

Example 6

Synthesis of 2-Amino-4-hydroxy-4-(3-indolylmethyl)hexanoic Acid 6

[Chemical formula 10]

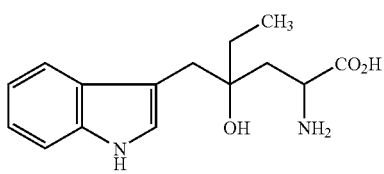

In a similar manner to Example 5 except that 3-(3-indolyl)-2-ethyl-1-propene was used instead of 3-(3-indolyl)-2-methyl-1-propene, 2-amino-4-hydroxy-4-(3-indolylmethyl)hexanoic acid was obtained with a yield of 41.1% as light brown powder (Compound No. 6 in Table 1).

MS Spectrum—

ESI-MS: 277.25 (M+H)$^+$, 275.16 (M−H)$^-$.

NMR Spectrum—

$^1$H-NMR (CD$_3$OD, 400 MHz) δppm:

[Isomer A (60%)] 0.95 (3H,t), 1.65-1.75 (2H,m), 1.88 (1H, dd), 2.27 (1H,dd), 2.90-3.10 (2H,m), 3.91 (1H,dd), 6.92-7.01 (1H,m), 7.01-7.06 (1H,m), 7.12 (1H,s), 7.31 (1H,d), 7.60 (1H,d).

[Isomer B (40%)] 1.09 (3H,t), 1.50-1.60 (2H,m), 1.86 (1H, dd), 2.24 (1H,dd), 2.90-3.10 (2H,m), 3.71 (1H,dd), 6.92-7.01 (1H,m), 7.01-7.06 (1H,m), 7.23 (1H,s), 7.33 (1H,d), 7.57 (1H,d).

Degree of Sweetness—

About 500 times (compared with a 5% sugar solution).

Example 7

Synthesis of (2R,4R)-2-Amino-4-hydroxy-4-methylcarbamoyl-4-(3-indolylmethyl)butyric Acid 7

[Chemical formula 11]

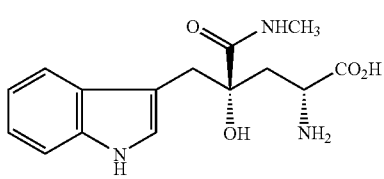

(2R,4R)-2-Benzyloxycarbonylamino-4-carboxy-4-(3-indolylmethyl-γ-butyrolactone in an amount of 767 mg (1.88 mmol), which was obtained by benzyloxycarbonylation and lactonization of (2R,4R)-monatin was dissolved in a mixed solvent containing 10 ml of THF, 10 ml of dichloromethane, and 10 ml of dimethylformamide (DMF), and the solution was maintained at a temperature of 0° C. To the resulting reaction solution, 153 mg of methylamine hydrochloride (2.26 mmol), 0.32 ml of triethylamine (2.26 mmol), 346 mg of 1-hydroxybenzotriazole hydrate (2.26 mmol) and 433 mg of 1-ethyl-3-(3-dimethylaminopropyl)carbodiimide hydrochloride (2.26 mmol) were added, and the solution was stirred overnight at room temperature. The reaction solution was then vacuum concentrated, and 50 ml of water was added to the residue followed by extraction with 50 ml of ethyl acetate (twice). The organic layer was washed with 30 ml of a 5% aqueous citric acid solution (twice), with 30 ml of a saturated salt solution (once), with 30 ml of a 5% aqueous sodium bicarbonate solution (twice), and with 30 ml of a saturated salt solution (once). The organic layer was dried over anhydrous magnesium sulfate, and the magnesium sulfate was removed by filtration, followed by vacuum concentration of the filtrate. The residue was purified on PTLC resulting in 897 mg of (2R,4R)-2-benzyloxycarbonylamino-4-methylcarbamoyl-4-(3-indolylmethyl)-γ-butyrolactone.

The aforementioned (2R,4R)-2-benzyloxycarbonylamino-4-methylcarbamoyl-4-(3-indolylmethyl)-γ-butyrolactone in an amount of 897 mg was dissolved in 40 ml of methanol, and 400 mg of 10% Pd—C was added thereto. Reduction was performed at room temperature in an atmosphere of hydrogen at ordinary pressure for 1 hour. After removing the catalyst by filtration, the reaction solution was vacuum concentrated. The residue was dissolved in 15 ml of ethanol, and 1.9 ml of a 2 N sodium hydroxide solution was added followed by stirring for a while. The reaction solution was vacuum concentrated and the residue was dissolved in 5 ml of water. The pH of the resulting solution was adjusted with a 2 N hydrochloric acid solution to be slightly acidic. Ethanol was then added and the deposited crystals were filtered resulting in 360 mg of (2R,4R)-2-amino-4-hydroxy-4-methylcarbamoyl-4-(3-indolylmethyl)butyric acid (1.18 mmol) as a crystal (Compound No. 7 in Table 1).

MS Spectrum—

ESI-MS: 306.35 (M+H)$^+$, 304.06 (M−H)$^-$.

NMR Spectrum—

$^1$H-NMR (CD$_3$OD, 400 MHz) δppm: 2.08 (1H,dd), 2.60 (3H,s), 2.62 (1H,dd), 3.15 (1H,d) 3.03 (1H,d), 3.63 (1H,m), 6.95-6.99 (1H,m), 7.03-7.07 (1H,m), 7.11 (1H,s), 7.58 (1H, d).

Degree of Sweetness—

About 200 times (compared with a 5% sugar solution).

Example 8-1

Synthesis of (2R,4R)-2-Amino-4-hydroxy-4-ethylcarbamoyl-4-(3-indolylmethyl)butyric Acid 8

[Chemical formula 12]

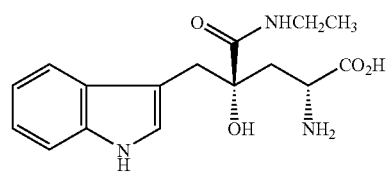

In a similar manner to Example 7 except that ethylamine hydrochloride was used instead of methylamine hydrochloride, (2R,4R)-2-amino-4-hydroxy-4-ethylcarbamoyl-4-(3-indolylmethyl)butyric acid was obtained with a yield of 56.6% as a crystal (Compound No. 8 in Table 1).

MS Spectrum—

ESI-MS: 320.21 (M+H)$^+$, 318.21 (M−H)$^-$.

NMR Spectrum—

$^1$H-NMR (CD$_3$OD, 400 MHz) δppm: 0.85 (3H,t), 2.10 (1H,dd), 2.61 (1H,dd), 3.00-3.18 (3H,m), 3.27 (1H,d), 3.66 (1H,m), 6.94-6.99 (1H,m), 7.01-7.07 (1H,m), 7.10 (1H,s), 7.29 (1H, d), 7.60 (1H,d).

Degree of Sweetness—

About 1600 times (compared with a 5% sugar solution).

Example 8-2

Synthesis of Racemate of 2-Amino-4-hydroxy-4-ethylcarbamoyl-4-(3-indolylmethyl)butyric Acid In a similar manner to Example 5 except that 3-(3-indolyl)-2-ethylcarbamoyl-1-propene was used instead of 3-(3-indolyl)-2-methyl-1-propene, 2-amino-4-hydroxy-4-ethylcarbamoyl-4-(3-indolylmethyl)butyric acid was obtained with a yield of 63.5% as light brown powder.

MS Spectrum—

ESI-MS: 320.21 (M+H)$^+$, 318.21 (M−H)$^-$.

NMR Spectrum—

$^1$H-NMR (CD$_3$OD, 400 MHz) δppm:

[Isomer A (60%)]: the same as the aforementioned (2R,4R)-2-amino-4-hydroxy-4-ethylcarbamoyl-4-(3-indolylmethyl) butyric acid.

[Isomer B (40%)] 0.84 (3H,t), 2.15 (1H,dd), 2.40 (1H,dd), 3.00-3.18 (3H,m), 3.28 (1H,d), 3.45 (1H,m), 6.94-6.99 (1H, m), 7.01-7.07 (1H,m), 7.10 (1H,s), 7.30 (1H,d), 7.60 (1H,d).

Numerous modifications and variations on the present invention are possible in light of the above teachings. It is, therefore, to be understood that within the scope of the accompanying claims, the invention may be practiced otherwise than as specifically described herein.

The invention claimed is:

1. An isolated amino acid derivative, or salt form thereof, represented by formula (1):

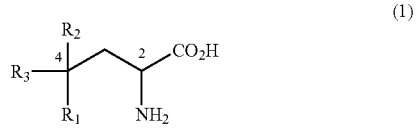

(1)

wherein
R$_1$ represents any substituent selected from the group consisting of a hydrogen atom, a hydroxyl group, an alkyl group having 1 to 3 carbon atoms, an alkoxy group having 1 to 3 carbon atoms, and a hydroxylalkyl group having 1 to 3 carbon atoms;
R$_2$ represents any substituent selected from the group consisting of an alkyl group having 1 to 3 carbon atoms, a hydroxylalkyl group having 1 to 3 carbon atoms, a carbamoyl group, a carbamoyl group having an alkyl having 1 to 3 carbon atoms, and a carboxyl group; and
R$_3$ represents a substituent represented by formula (2):

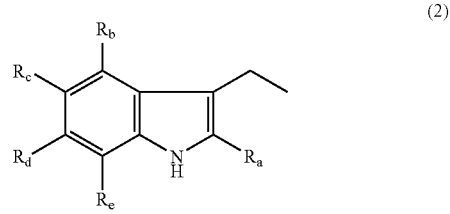

(2)

wherein
R$_a$, R$_b$, R$_c$, R$_d$, and R$_e$ each independently represent any substituent selected from the group consisting of a hydrogen atom, a hydroxyl group, an alkyl group having 1 to 3 carbon atoms, and an alkoxy group having 1 to 3 carbon atoms;
R$_b$ and R$_c$, and/or R$_d$ and R$_e$ may together form an alkylene group having 1 to 4 carbon atoms, respectively,
with the proviso that however compounds concurrently having R$_1$ of a hydroxyl group, R$_2$ of a carboxyl group, and R$_3$ of a 3-indolylmethyl group in the formula (1) are excluded from said derivative.

2. The derivative, or salt form thereof, according to claim 1, wherein
R$_1$ represents a substituent selected from the group consisting of a hydrogen atom, a hydroxyl group, a methyl group, and a methoxy group;
R$_2$ represents a substituent selected from the group consisting of a methyl group, an ethyl group, a hydroxymethyl group, a 1-hydroxyethyl group, a 2-hydroxyethyl group, a carbamoyl group, an N-methylcarbamoyl group, an N-ethylcarbamoyl group, and a carboxyl group; and
R$_3$ represents a substituent selected from the group consisting of a 3-indolylmethyl group, a 3-(5-methylindolyl)methyl group, a 3-(6-methylindolyl)methyl group, a 3-(5-hydroxyindolyl)methyl group, or a 3-(6-chloroindolyl)methyl group.

3. The derivative, or salt form thereof, according to claim 2, wherein the configuration of the carbon atom at position 2 is any one of (R), (S) and (RS).

4. The derivative, or salt form thereof, according to claim 2, wherein the configuration of the carbon atom at position 4 is any one of (R), (S) and (RS).

5. The derivative, or salt form thereof, according to claim 1, wherein the configuration of the carbon atom at position 2 is any one of (R), (S) and (RS).

6. The derivative, or salt form thereof, according to claim 1, wherein the configuration of the carbon atom at position 4 is any one of (R), (S) and (RS).

7. The derivative, or salt form thereof, according to claim 1, wherein
R$_1$ represents a hydrogen atom;
R$_2$ represents a carboxyl group; and
R$_3$ represents a 3-indolylmethyl group.

8. The derivative, or salt form thereof, according to claim 1, wherein
R$_1$ represents a hydroxyl group;
R$_2$ represents a carboxyl group; and
R$_3$ represents a 3-(6-methylindolyl)methyl group.

9. The derivative, or salt form thereof, according to claim 1, wherein
$R_1$ represents a hydroxyl group;
$R_2$ represents a hydroxymethyl group; and
$R_3$ represents a 3-indolylmethyl group.

10. The derivative, or salt form thereof, according to claim 1, wherein
$R_1$ represents a hydroxyl group;
$R_2$ represents a methyl group; and
$R_3$ represents a 3-indolylmethyl group.

11. The derivative, or salt form thereof, according to claim 1, wherein
$R_1$ represents a hydroxyl group;
$R_2$ represents an ethyl group; and
$R_3$ represents a 3-indolylmethyl group.

12. The derivative, or salt form thereof, according to claim 1, wherein
$R_1$ represents a hydroxyl group;
$R_2$ represents a carbamoyl group; and
$R_3$ represents a 3-indolylmethyl group.

13. The derivative, or salt form thereof, according to claim 1, wherein
$R_1$ represents a hydroxyl group;
$R_2$ represents an N-methylcarbamoyl group; and
$R_3$ represents a 3-indolylmethyl group.

14. The derivative, or salt form thereof, according to claim 1, wherein
$R_1$ represents a hydroxyl group;
$R_2$ represents an N-ethylcarbamoyl group; and
$R_3$ represents a 3-indolylmethyl group.

15. The derivative, or salt form thereof, according to claim 1, wherein
$R_1$ represents a hydrogen atom, or a hydroxyl group;
$R_2$ represents a substituent selected from the group consisting of a methyl group, an ethyl group, a hydroxymethyl group, a carbamoyl group, an N-methylcarbamoyl group, an N-ethylcarbamoyl group, and a carboxyl group; and
$R_3$ represents a substituent selected from the group consisting of a 3-indolylmethyl group, or a 3-(6-methylindolyl)methyl group.

16. The derivative, or salt form thereof, according to claim 1, wherein the form of said salt is selected from the group consisting of an alkali metal salt, an alkaline earth metal salt, an ammonium salt, an amino acid salt, an inorganic acid salt, an organic acid salt, and a salt with at least one other sweetening ingredient.

17. A sweetening composition, comprising the derivative, or salt form thereof, according to claim 1 as an effective ingredient and at least one carrier, bulking agent, or mixture thereof.

18. The sweetening composition according to claim 17, further comprising at least one additional sweetener selected from the group consisting of saccharin, acesulfame, cyclamic acid and glycyrrhizic acid.

19. The sweetening composition according to claim 17, wherein said derivative, or salt form thereof, is present at a concentration ranging from 0.0006 to 0.15% by weight.

20. The sweetening composition according to claim 17, wherein said derivative, or salt form thereof, is present at a concentration ranging from 0.003 to 0.075% by weight.

21. A food or beverage comprising the sweetening composition of claim 17.

22. A method of increasing the sweetness of a food or beverage comprising mixing an effective amount of the sweetening composition of claim 17 with a food, beverage, or precursor thereof.

* * * * *